(12) United States Patent
Lor et al.

(10) Patent No.: US 7,862,777 B2
(45) Date of Patent: Jan. 4, 2011

(54) COAXIAL TISSUE BLOCK PUNCHER SET

(76) Inventors: Shih-Chung Lor, 3F.-1No. 7, Wucyuan 1st Rd., Sinjhuang City, Taipei County 242 (TW); Chin-Tsung Lor, 3F.- 1No. 7, Wucyuan 1st Rd., Sinjhuang City, Taipei County 242 (TW); Kuo-Lung Lor, 3F.-1No. 7, Wucyuan 1st Rd., Sinjhuang City, Taipei County 242 (TW)

( * ) Notice: Subject to any disclaimer, the term of this patent is extended or adjusted under 35 U.S.C. 154(b) by 433 days.

(21) Appl. No.: 12/052,785

(22) Filed: Mar. 21, 2008

(65) Prior Publication Data

US 2009/0239294 A1 Sep. 24, 2009

(51) Int. Cl.
*B01L 3/00* (2006.01)
(52) U.S. Cl. ....................................................... 422/99
(58) Field of Classification Search .................... 422/99
See application file for complete search history.

*Primary Examiner*—Walter D Griffin
*Assistant Examiner*—Bobby Ramdhanie
(74) *Attorney, Agent, or Firm*—Shimokaji & Associates, P.C.

(57) ABSTRACT

A coaxial tissue block puncher set comprises a carrier mechanism, the first, second and third operating mechanisms being respectively installed at proper positions thereon, while each of the operating mechanisms respectively has a base and a lifting unit being movingly installed on the base, wherein lifting unit of the first operating mechanism is movingly installed with a first punch needle tube, lifting unit of the second operating mechanism being movingly installed with a second punch needle tube is pierced through the first punch needle tube, and lifting unit of the third operating mechanism being movingly installed with a thimble is pierced through the second punch needle tube. Therefore, user is able to punch-extract relevant pathological paraffin and put to relevant position in the empty block thereby forming a tissue array without the need for tedious manual methods thus achieving the effectiveness of fastness, precision and easy operation, etc.

3 Claims, 9 Drawing Sheets

COAXIAL TISSUE BLOCK PUNCHER SET

FIELD OF THE INVENTION

The invention is related to a coaxial tissue block puncher set, more particularly to the one having the effectiveness of fastness, precision and easy operability to punch-extract tissue blocks.

BACKGROUND OF THE INVENTION

The conventional way of extracting pathological tissue block is generally by manual punching (or cutting) for succeeding analysis, research or testing;

Nonetheless, the current manual punching (or cutting) methods for extracting pathological tissue blocks are usually affected by the unstable factors caused by humans such as that too much force, inaccurate visual measurement or different textures and portions of the pathological tissue block make the manually punched (cut) pathological tissue block become oblique or appear different sizes. The precious pathological tissue blocks extracted by manual methods are tended to be damaged due to too much force exerted or imprecise punching or (cutting) thereby resulting in the imprecise analysis, research or testing and the process is very time consuming so as to prolong the pathological analysis research schedule.

SUMMARY OF THE INVENTION

Therefore, the present invention is mainly purposed to allow user to be able to punch-extract relevant pathological tissue block and put to relevant position in the empty block thereby forming a tissue array so as to achieve the effectiveness of fastness, precision and easy operation, etc. The tissue array is a method for relocating multiple tissues from conventional pathological paraffin blocks so that tissues from multiple patients can be seen on a same slide to allow for simultaneous pathological analysis.

To achieve said purpose, the present invention discloses a coaxial tissue block puncher set comprising a carrier mechanism, the first, second and third operating mechanisms are respectively installed at proper positions thereon, while each of the operating mechanisms respectively has a base, and a lifting unit being movingly installed on the base, the lifting unit of the first operating mechanism is movingly installed with a first punch needle tube, the lifting unit of the second operating mechanism being movingly installed with a second punch needle tube is pierced through the first punch needle tube, and the lifting unit of the third operating mechanism being movingly installed with a thimble is pierced through the second punch needle tube.

Further, the present invention can also be another embodiment of coaxial tissue block puncher set to comprise a first punch needle tube having a first holding portion at one end thereof and a first attracting piece on the top end thereof; a second punch needle tube being pierced through first punch needle tube having a second holding portion relative to first holding portion at one end thereof and a second attracting piece respectively at the top and bottom ends thereof; and a thimble being pierced through said second punch needle tube having a third holding portion relative to second holding portion at one end thereof and a third attracting piece at the bottom end thereof.

BRIEF DESCRIPTION OF THE DRAWINGS

FIGS. 5-1~5-8 are cross-sectional views showing the usage status of the first embodiment of the invention.

FIGS. 8-1~8-9 are cross-sectional views showing the usage status of the second embodiment of the invention.

DETAILED DESCRIPTION OF THE PREFERRED EMBODIMENTS

FIGS. 1, 2, 3 and 4 are respectively a perspective outlook schematic view of the first embodiment of the invention, the first perspective decomposition schematic view showing the first operating mechanism in the first embodiment of the invention, a perspective decomposition schematic view showing the second operating mechanism in the first embodiment of the invention and a perspective decomposition schematic view showing the third operating mechanism in the first embodiment of the invention. As shown by the Figs., the coaxial tissue block puncher set of the present invention comprises a carrier mechanism 10, a first operating mechanism 11, a second operating mechanism 12 and a third operating mechanism 13.

Said carrier mechanism 10 can be mounted on a translational mechanism (not shown in the Fig.).

Figure 1:
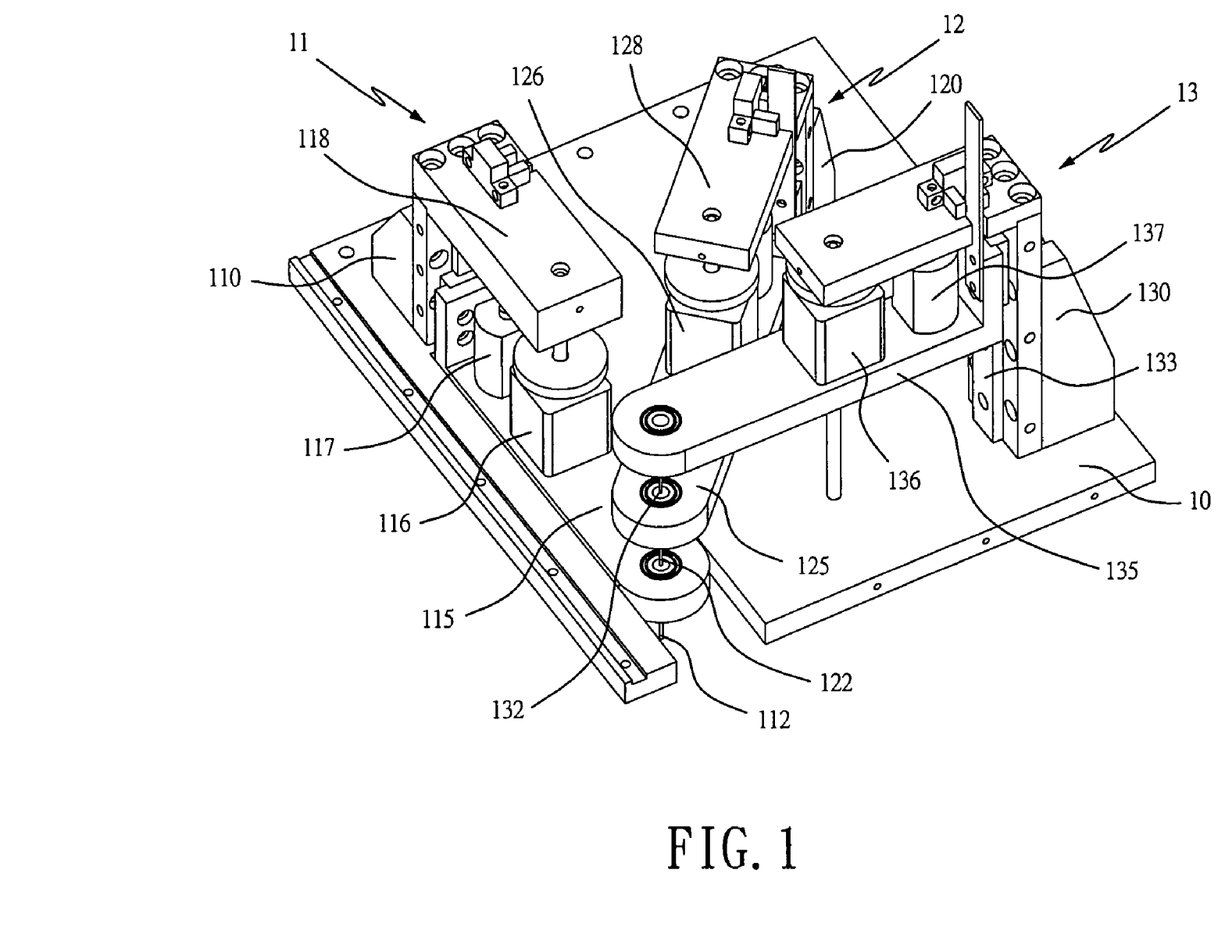
FIG. 1 is a perspective schematic view of the first embodiment of the invention.
Figure 2:
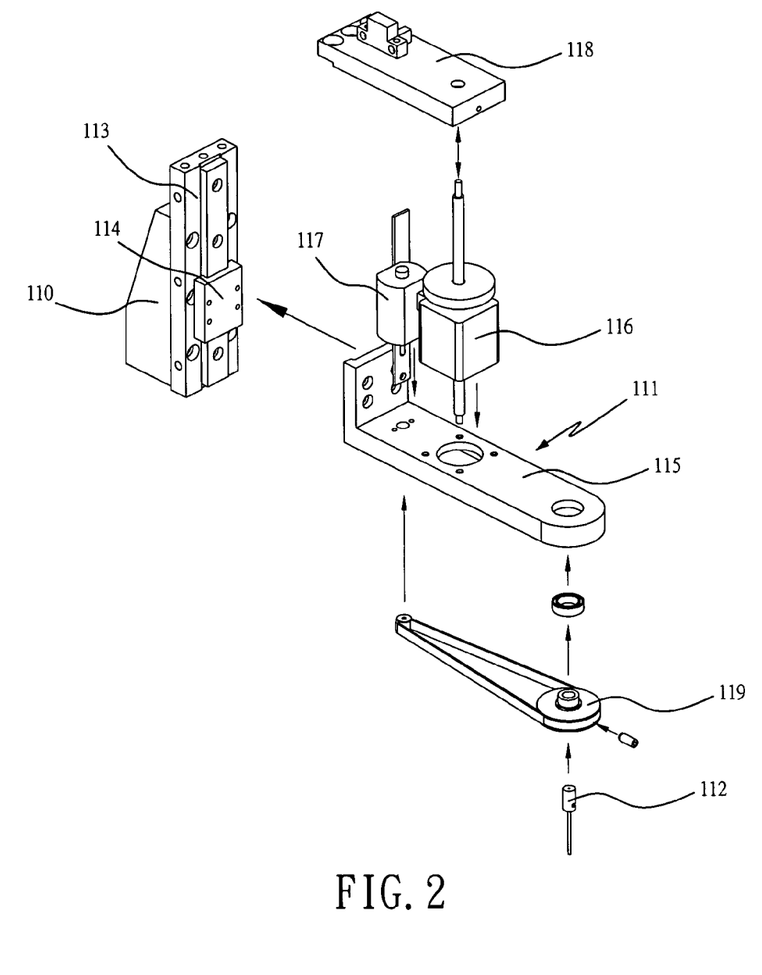
FIG. 2 is a perspective decomposition schematic view showing the first operating mechanism in the first embodiment of the invention.

The first operating mechanism 11 being installed on a proper position at said carrier mechanism 10 at least comprises a base 110, a lifting unit 111 being movingly installed thereon and a first punch needle tube 112 is installed on the lifting unit 111, wherein the surface of base 110 is installed with a guide rail 113 at one side, and the lifting unit 111 having a slide 114 being movingly installed on guide rail 113 is matched with a movable arm 115 being installed with a first actuating component 116 thereon and a second actuating component 117 thereon, a top cover 118 being installed on the end surface of base 110 is combined with the first actuating component 116, and a transmission piece 119 is connected with the second actuating component 117, while said first punch needle tube 112 is connected with the transmission piece 119 (as shown in FIG. 2).

Figure 3:
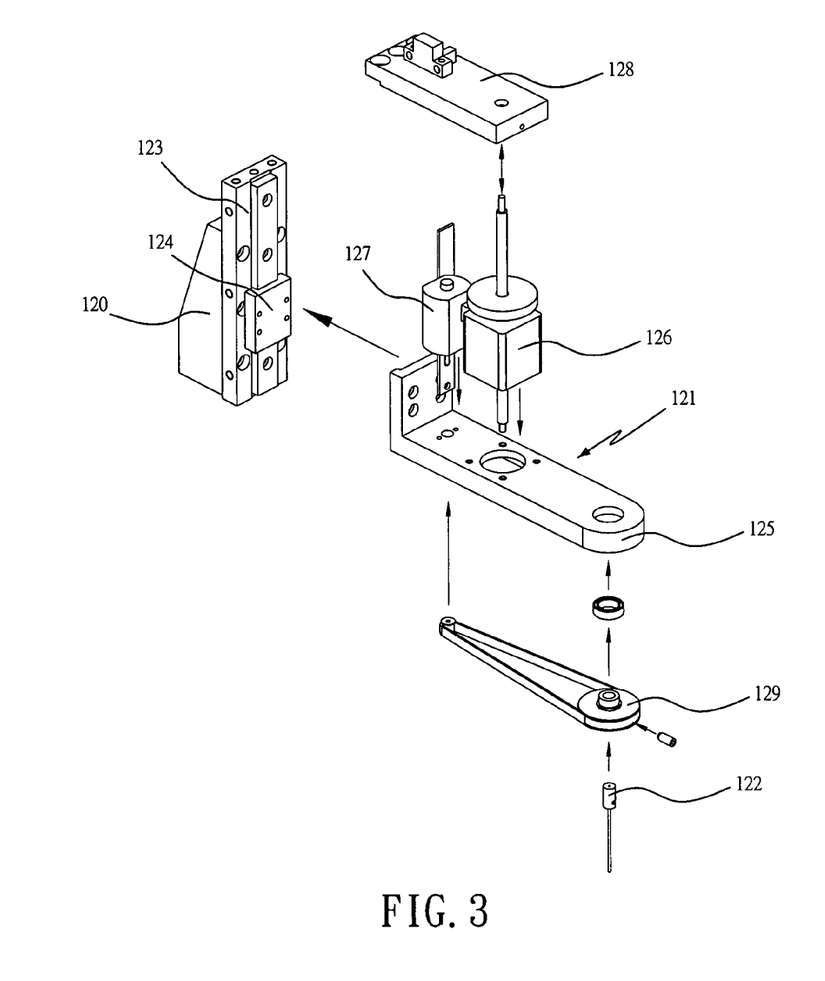
FIG. 3 is a perspective decomposition schematic view showing the second operating mechanism in the first embodiment of the invention.

The second operating mechanism 12 is installed at the vicinity of the first operating mechanism 11 on said carrier mechanism 10, wherein the second operating mechanism 12 at least has a base 120, a lifting unit 121 is movingly installed thereon, a second punch needle tube 122 is movingly installed on the lifting unit 121 and pierced through first punch needle tube 112, and the surface of base 120 is installed with a guide rail 123 at one side, the lifting unit 121 having a slide 124 being movingly installed on guide rail 123 is matched with a movable arm 125 being installed with a first actuating component 126 thereon and a second actuating component 127 thereon, a top cover 128 being installed on the end surface of base 120 is combined with the first actuating component 126, and a transmission piece 129 is connected with the second actuating component 127, while said second punch needle tube 122 is connected with the transmission piece 129 (as shown in FIG. 3).

Figure 4:
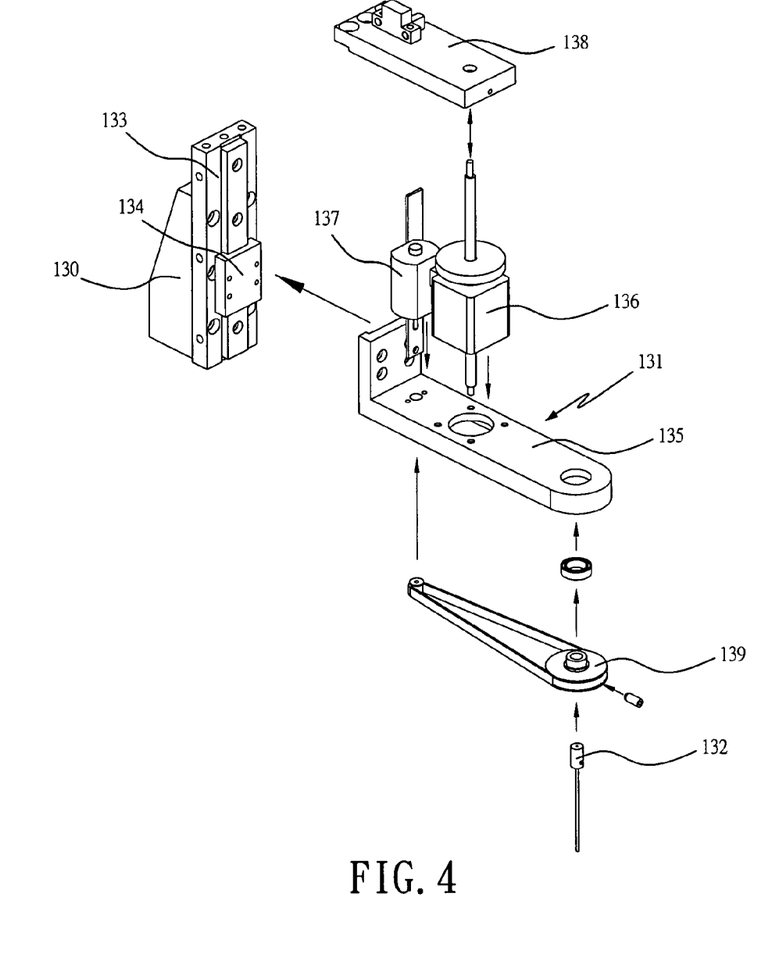
FIG. 4 is a perspective decomposition schematic view showing the third operating mechanism in the first embodiment of the invention.

The third operating mechanism 13 is installed at the vicinity of the second operating unit 12 on said carrier mechanism 10, wherein the third operating mechanism 13 at least has a base 130, a lifting unit 131 is movingly installed thereon, a thimble 132 is movingly installed on the lifting unit 131 and pierced through second punch needle tube 122, and the base 130 is installed with a guide rail 133 at one side, the lifting unit 131 having a slide 134 being movingly installed on guide rail 133 is matched with a movable arm 135 being installed with a first actuating component 136 thereon and a second actuating component 137 thereon, a top cover 138 being installed on the end surface of base 130 is combined with the first actuating component 136, and a transmission piece 139 is connected with the second actuating component 127, while said thimble 132 is connected with the transmission piece 139 (as shown in FIG. 4). As such, the brand new coaxial tissue block puncher set is constituted by above described structures.

FIGS. 5-1~5-8 are cross-sectional views showing the usage status of the first embodiment of the invention. Regarding operations for the present invention as shown in the Figs. (simultaneously referring to FIG. 1), the carrier mechanism 10 can be matched with a translation mechanism (not shown in the Fig.) for necessary operations, while the length of first punch needle tube 112 can be set to smaller than the one of second punch needle tube 122 by about 10 mm, and the length of second punch needle tube 122 can be set equal to the one of thimble 132;

In usage, the carrier mechanism 10 is translated on the empty block 20 to allow the movable arm 125 of second operating mechanism 12 on base 120 to move downward through the first actuating component 126 thereby allowing second punch needle tube 122 to insert into the empty block 20 from top surface whereof and further drive transmission piece 129 through second actuating component 127 to allow second punch needle tube 122 to rotate above empty block 20 for easy-extracting paraffin 202, wherein the paraffin 202 being put into second punch needle tube 122 drives the thimble 132 upward.

Next, the movable arm 125 is moved upward through first actuating component 126 to form a cavity 201 on the empty block 20, then the movable arm 135 of the third operating mechanism 13 on base 130 is moved downward through first actuating component 136 to drive thimble 132 to remove paraffin 202 inside second punch needle tube 122 as a waste;

After cavity 201 on the empty block 20 is made, the carrier mechanism 10 is translated to corresponding tissue block 30 to allow the movable arm 115 of the first operating mechanism 11 on base 110 to move downward through first actuating component 116 thereby allowing the first punch needle tube 112 to insert into tissue block 30 from top surface whereof and further drive transmission piece 119 through second actuating component 117 to allow first punch needle tube 112 to rotate above tissue block 30 for easy-extracting pathological paraffin 301. The pathological paraffin 301 being put into first punch needle tube 112 drives the second punch needle tube 122 and thimble 132 upward. Next, the movable arm 115 is moved upward through actuating component 116 to allow the pathological paraffin 301 to remain inside the first punch needle tube 112 and translate the carrier mechanism 10 above the corresponding cavity 201 on the empty block 20, then the movable arm 135 of the third operating mechanism 13 on base 130 is moved downward through first actuating component 136 to drive thimble 132 to put pathological paraffin 301 inside first punch needle tube 112 into the cavity 201.

The above said procedures are then repeated completely to form the tissue array on the empty block for succeeding analysis, research or testing to let users be able to punch-extract relevant pathological tissue paraffin and put to relevant position in the empty block thereby forming a tissue array without the need for tedious manual methods thus achieving the effectiveness of fastness, precision and easy operation, etc. The tissue array is a method for relocating multiple tissues from conventional pathological paraffin blocks so that tissues from multiple patients can be seen on a same slide to allow for simultaneous pathological analysis.

Figure 6:
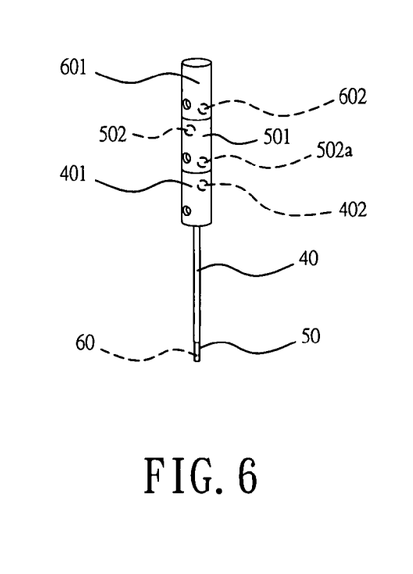
FIG. 6 is a perspective outlook schematic view of the second embodiment of the invention.
Figure 7:
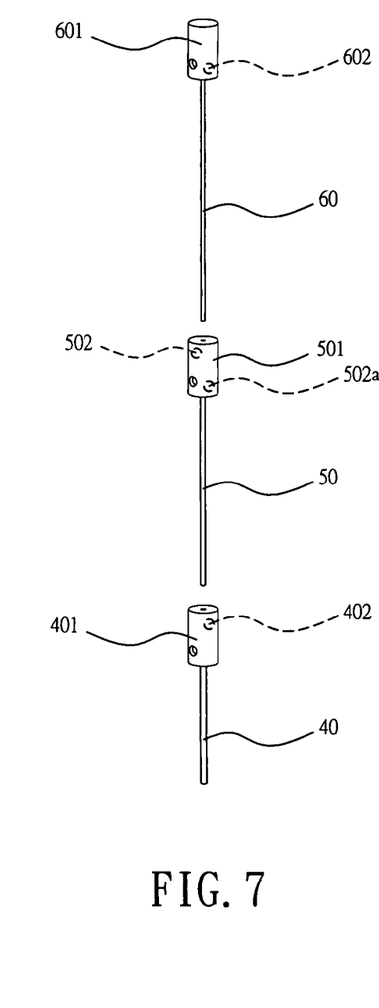
FIG. 7 is a perspective decomposition schematic view of the second embodiment of the invention.
Figure 51:
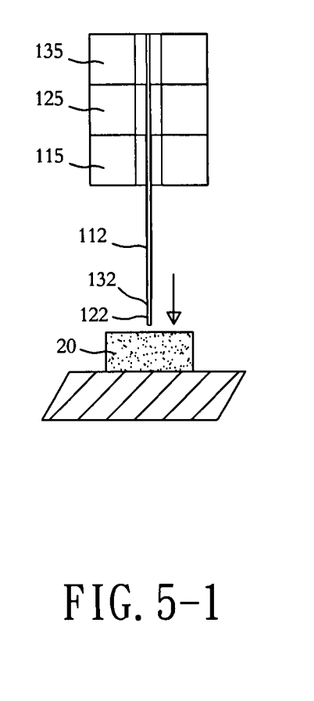
Figure 52:
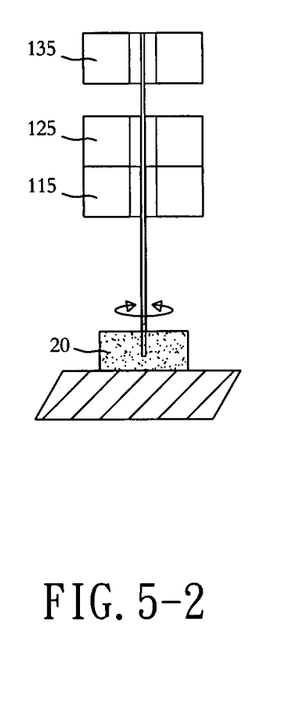
Figure 53:
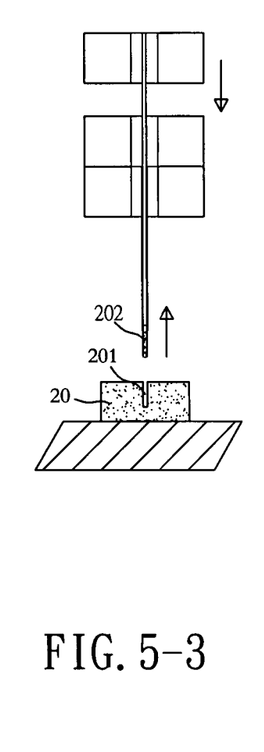
Figure 54:
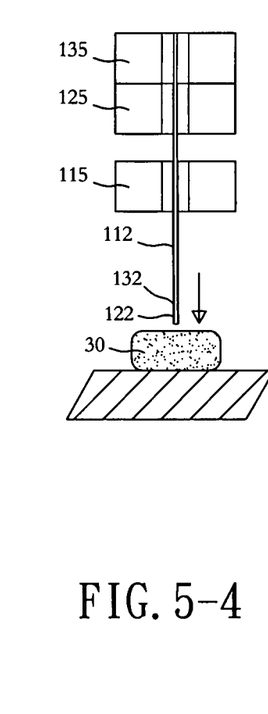
Figure 55:
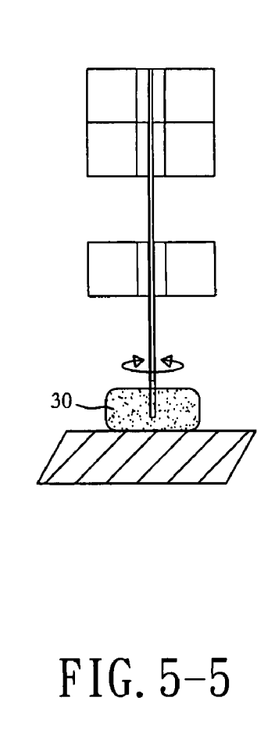
Figure 56:
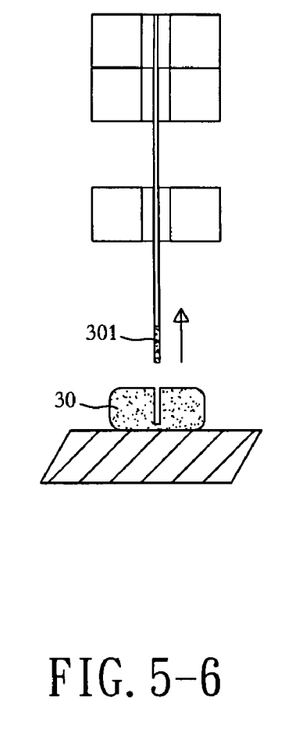
Figure 57:
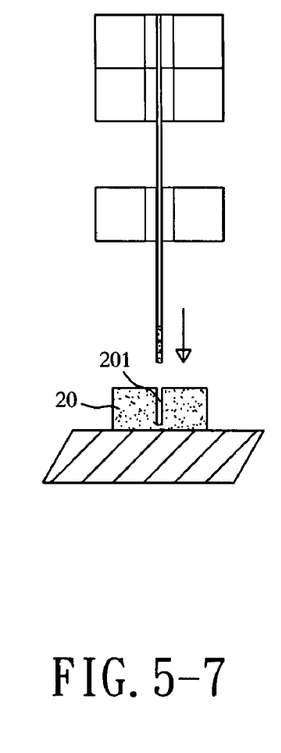
Figure 58:
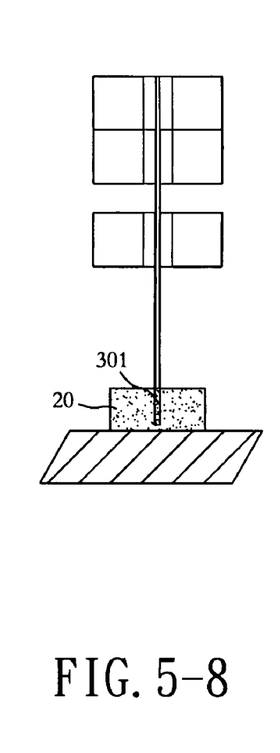
Figure 81:
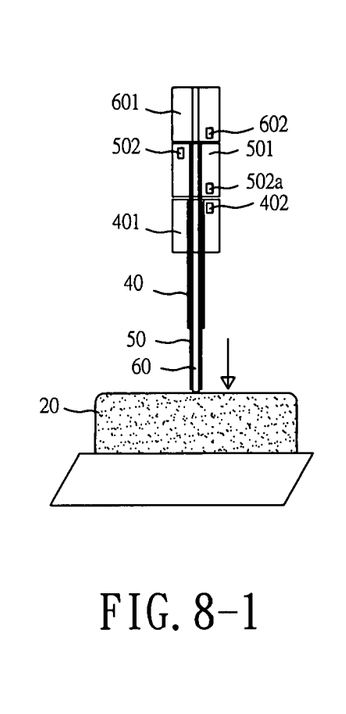
Figure 82:
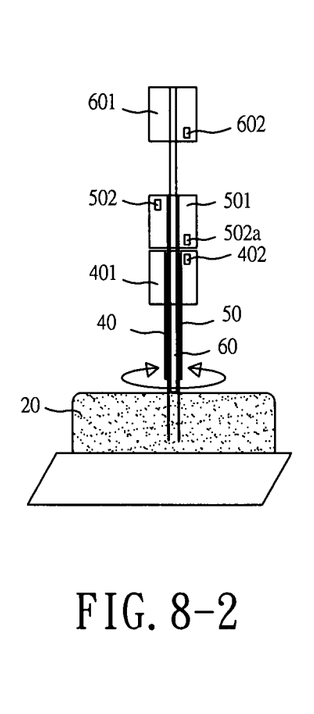
Figure 83:
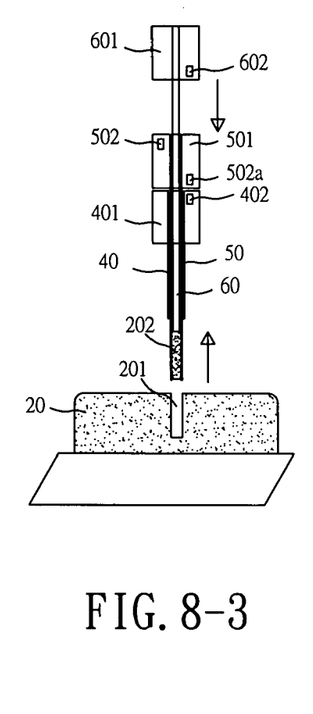
Figure 84:
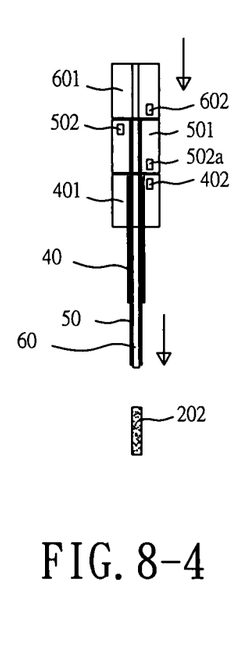
Figure 85:
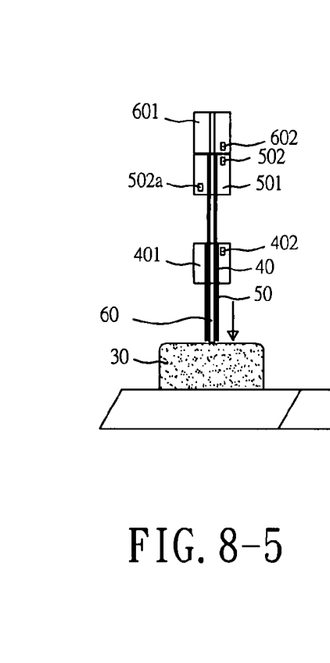
Figure 86:
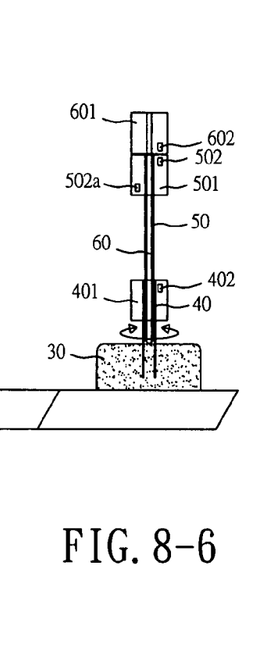
Figure 87:
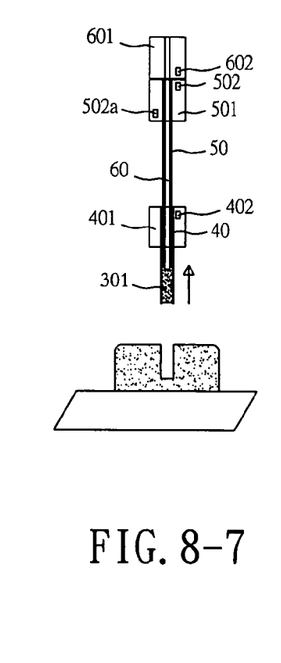
Figure 88:
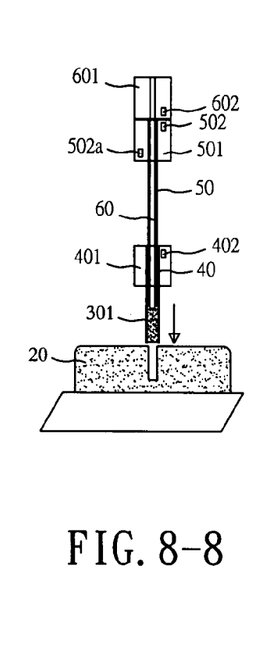
Figure 89:
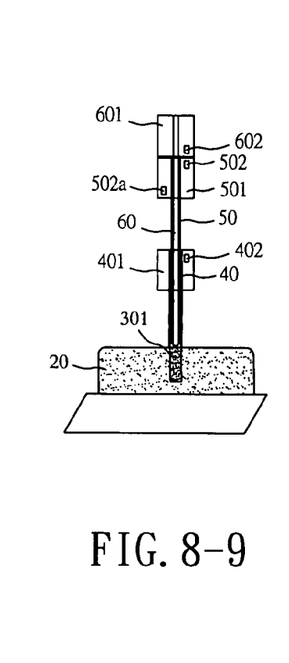

FIGS. 6 and 7 are respectively a perspective outlook schematic view of the second embodiment of the invention and the perspective decomposition view of the second embodiment of the invention. Beside of the said structure type of the first embodiment, the present invention can be another coaxial tissue block puncher set to comprise a first punch needle tube 40 having a first holding portion 401 at one end thereof and a first attracting piece 402 on the top end thereof; a second punch needle tube 50 being pierced through first punch needle tube 40 having a second holding portion 501 relative to first holding portion 401 at one end thereof and a second attracting piece 502 respectively at the top and bottom ends thereof; and a thimble 60 being pierced through second punch needle tube 50 having a third holding portion 601 relative to said second holding portion 501 at one end thereof and a third attracting piece 602 at the bottom end thereof; wherein the length of first punch needle tube 40 is smaller than the one of second punch needle tube 50, and the length of second punch needle tube 50 is smaller than thimble 60; while the first, second and third attracting pieces 402, 502, 602 can be magnets to allow user to rotate the first holding portion 401, second holding portion 501 and third holding portion 601, wherein the up and down movements of first punch needle tube 40, second punch needle tube 50 and thimble 60 are controlled by whether the first, second and third attracting pieces 402, 502, 602 are relatively attracted or not.

FIGS. 8-1~8-9 are cross-sectional views showing the usage status of the second embodiment of the invention. In usage as shown in the Figs., the first punch needle tube 40, second punch needle tube 50 and thimble 60 are hand held by the user to translate to above the empty block 20. Next, second holding portion 501 is rotated to allow second attracting piece 502 not to attractingly attach with the third attracting piece 602 at middle to bottom end of the third holding portion 601, but to allow attracting piece 502*a* at bottom end thereof to attractingly attach with first attracting piece 402 at middle to top end of first holding portion 401 thereby moving second punch needle tube 50 downward to insert into empty block 20 from top surface whereof, wherein second punch needle tube 50 is rotated above empty block 20 for easy-extracting paraffin 202 by rotating second holding portion 501 and first holding portion 401 together, wherein the paraffin 202 being put into second punch needle tube 50 drives the thimble 60 upward; then second punch needle tube 50 along with first punch needle tube 40 and thimble 60 are retracted away from empty block 20 to leave a required cavity 201 on empty block 20; after that, thimble 60 is moved downward inside second punch needle tube 50 so as to remove paraffin 202 inside second punch needle tube 50 as a waste.

After cavity 201 on the empty block 20 is made, the first punch needle tube 40, second punch needle tube 50 and thimble 60 are translated to above corresponding tissue block 30 and second holding portion 501 is rotated to allow second attracting piece 502 at top end thereof to attractingly attach with the third attracting piece 602 at middle to bottom end of third holding portion 601 while attracting piece 502a is not allowed to attractively attach with first attracting piece 402 at top end of first holding portion 401 thereby allowing first punch needle tube 40 to insert into tissue block 30 from top surface whereof. Next, first punch needle tube 40 above tissue block 30 is rotated for easy-extracting pathological paraffin 301 by rotating the first holding portion 401, wherein the pathological paraffin 301 being put into first punch needle tube 40 that drives the second punch needle tube 50 and thimble 60 upward; After that, first punch needle tube 40 along with second needle tube 50 and thimble 60 are retracted away from pathological tissue 30 to allow pathological paraffin 301 to remain inside the first punch needle tube 40 and first punch needle tube 40, second punch needle tube 50 and thimble 60 are translated above the corresponding cavity 201 on the empty block 20 so as to allow thimble 60 to move downward inside first punch needle tube 40 thereby driving thimble 60 to put pathological paraffin 301 inside first punch needle tube 40 into cavity 201, and similarly, the above said procedures are then repeated completely to form the tissue array on the empty block for succeeding analysis, research or testing to let users be able to punch-extract relevant pathological tissue paraffin and put to relevant position in the empty block thereby forming a tissue array with the effectiveness of fastness, precision and easy operation, etc. The tissue array is a method for relocating multiple tissues from conventional pathological paraffin blocks so that tissues from multiple patients can be seen on a same slide to allow for simultaneous pathological analysis.

As summarized from above descriptions, the coaxial tissue block puncher set of the present invention allows the user to punch-extract relevant pathological tissue block and put to the relevant positions in the empty block thereby forming a tissue array to achieve the effectiveness of fastness, precision and easy operation, wherein the present invention is more progressive, practical and conforming to meet user demands, therefore, it has conformed to the key requirements for patent application which is applied according to the law herein.

As the above descriptions are only the preferred embodiments of the invention, they shall not be used to limit the claimed scopes of the invention. Hence, all simple equivalent variations and modifications based on the claims and descriptions of the invention shall be still considered to be included in the patent covering scope of the invention.

What is claimed is:

1. A coaxial tissue block puncher set includes:

A first punch needle tube having a first holding portion at one end thereof and a first attracting piece on the top end thereof;

A second punch needle tube being pierced through first punch needle tube having a second holding portion relative to first holding portion at one end thereof and a second attracting piece respectively at the top and bottom ends thereof; and A thimble being pierced through said second punch needle tube having a third holding portion relative to second holding portion at one end thereof and a third attracting piece at the bottom end thereof.

2. The coaxial tissue block puncher set as claimed in claim 1, wherein the first, second and third attracting pieces are magnets.

3. The coaxial tissue block puncher set as claimed in claim 1, wherein the length of first punch needle tube is smaller than the one of second punch needle tube, the inside diameter of first punch needle tube is the same as the outside diameter of second punch needle tube, the length of second punch needle tube is the same as the one of thimble, and the inside diameter of second punch needle tube is the same as the outside diameter of thimble.

* * * * *